United States Patent
Bentley et al.

(10) Patent No.: US 10,345,130 B2
(45) Date of Patent: Jul. 9, 2019

(54) AIRFLOW SENSOR WITH THERMAL CONDUCTIVITY AND DIFFUSIVITY SENSING

(71) Applicant: Honeywell International Inc., Morris Plains, NJ (US)

(72) Inventors: Ian Bentley, New Ipswich, NH (US); Lamar Floyd Ricks, Lewis Center, OH (US); Scott Edward Beck, Murphy, TX (US); Robert Higashi, Shorewood, MN (US)

(73) Assignee: Honeywell International Inc., Morris Plains, NJ (US)

( * ) Notice: Subject to any disclaimer, the term of this patent is extended or adjusted under 35 U.S.C. 154(b) by 241 days.

(21) Appl. No.: 15/358,970

(22) Filed: Nov. 22, 2016

(65) Prior Publication Data

US 2018/0143051 A1 May 24, 2018

(51) Int. Cl.
| | |
|---|---|
| *G01F 1/69* | (2006.01) |
| *G01F 1/688* | (2006.01) |
| *G01F 1/692* | (2006.01) |
| *G01F 1/708* | (2006.01) |
| *G01N 25/18* | (2006.01) |
| *G01N 25/20* | (2006.01) |

(52) U.S. Cl.
CPC .............. *G01F 1/69* (2013.01); *G01F 1/6888* (2013.01); *G01F 1/692* (2013.01); *G01F 1/7084* (2013.01); *G01N 25/18* (2013.01); *G01N 25/20* (2013.01)

(58) Field of Classification Search
CPC .......... G01F 1/69; G01F 1/692; G01F 1/6888; G01F 1/7084; G01N 25/18; G01N 25/20
See application file for complete search history.

(56) References Cited

U.S. PATENT DOCUMENTS

| | | | |
|---|---|---|---|
| 5,044,767 A | * | 9/1991 | Gustafsson ............ G01N 25/18 |
| | | | 374/43 |
| 5,080,495 A | | 1/1992 | Hashimoto et al. |
| 5,379,630 A | | 1/1995 | Lacey |
| 6,079,253 A | | 6/2000 | Bonne et al. |
| 7,003,418 B2 | * | 2/2006 | Bonne .................. G01N 27/185 |
| | | | 702/100 |
| 8,161,795 B2 | | 4/2012 | De Coulon et al. |
| 8,650,947 B2 | * | 2/2014 | Lopez .................. G01F 1/6842 |
| | | | 73/204.27 |

(Continued)

*Primary Examiner* — Freddie Kirkland, III
(74) *Attorney, Agent, or Firm* — Seager, Tufte, & Wickhem LLP

(57) ABSTRACT

Embodiments relate generally to a sensor for sensing a thermal property of a fluid and may comprise an upstream resistive element having a first resistance that changes with temperature; a downstream resistive element having a second resistance that changes with temperature, wherein the downstream resistive element is situated downstream of the upstream resistive element in the flow direction of the fluid; and at least one tail resistor configured to determine one or more thermal properties of the fluid, wherein the upstream resistive element and the downstream resistive element are operatively connected in a bridge circuit, wherein the at least one tail resistor is stable with temperature, and wherein the at least one tail resistor is electrically coupled to at least one of the upstream resistive element or the downstream resistive element.

20 Claims, 3 Drawing Sheets

(56) References Cited

U.S. PATENT DOCUMENTS

| | | | | |
|---|---|---|---|---|
| 2005/0049805 A1* | 3/2005 | Bonne | ................. | G01N 27/185 |
| | | | | 702/57 |
| 2011/0296910 A1* | 12/2011 | Lopez | ................. | G01F 1/6842 |
| | | | | 73/204.27 |
| 2017/0219402 A1* | 8/2017 | Milley | ................. | G01F 1/6845 |
| 2018/0224308 A1* | 8/2018 | Milley | ................. | G01F 1/6845 |

* cited by examiner

AIRFLOW SENSOR WITH THERMAL CONDUCTIVITY AND DIFFUSIVITY SENSING

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Fluid flow transducers are widely used to measure the flow of fluid materials. Flow sensors are used to sense fluid flow, and in some cases, provide flow signals that can be used for instrumentation and/or control. Flow sensors are used in a wide variety of applications including industrial applications, medical applications, engine control applications, military applications, and aeronautical applications, to name just a few. Gas flow transducers are used throughout the microelectronics industry, for example. The measurement and control of gas flows must be very precise in this industry. The vacuum technology used in the microelectronics industry requires small but precise gas flows. These small flows permit a flow meter to be located inside a gas delivery tube. Other industries require large gas consumptions. In such industries, a small fraction of the delivered gas may be routed through a bypass tube. The gas flow is often measured in this bypass tube, and the measured flow is then multiplied by the ratio of total gas flow to the gas flowing in the bypass tube. Fluid flow transducers are also used to measure the flow of liquid commodities. For example, chemical companies use fluid flow transducers to measure the flow of liquid reactants used in a chemical reaction. The precise measure of the flows of multiple reactants may be critical for maintaining a proper stoichiometric ratio for a reaction.

SUMMARY

In an embodiment, a sensor for sensing a thermal property of a fluid may comprise an upstream resistive element having a first resistance that changes with temperature; a downstream resistive element having a second resistance that changes with temperature, wherein the downstream resistive element is situated downstream of the upstream resistive element in the flow direction of the fluid; and at least one tail resistor configured to determine one or more thermal properties of the fluid, wherein the upstream resistive element and the downstream resistive element are operatively connected in a bridge circuit, wherein the at least one tail resistor is stable with temperature, and wherein the at least one tail resistor is electrically coupled to at least one of the upstream resistive element or the downstream resistive element.

In an embodiment, a method for determining one or more thermal property of a fluid may comprise assembling a bridge circuit comprising an upstream resistive element, a downstream resistive element, and at least one tail resistor electrically coupled to at least one of the upstream resistive element or the downstream resistive element; supplying power to the bridge circuit; feeding a fluid over the bridge circuit; measuring the voltage change at the tail resistor; and determining at least one thermal property of the fluid based on the measured voltage change.

In an embodiment, a flow sensor for sensing a fluid flow rate through a flow channel may comprise a heating element configured to be substantially in direct thermal coupling with the fluid flowing through the flow channel; an upstream resistive element having a first resistance that changes with temperature; a downstream resistive element having a second resistance that changes with temperature, wherein the downstream resistive element is situated downstream of the upstream resistive element in the flow channel; and at least one tail resistor configured to indicate one or more thermal properties of fluid flowing through the flow channel, wherein the upstream resistive element and the downstream resistive element are operatively connected in a bridge circuit; the at least one tail resistor is stable with temperature; and the at least one tail resistor is electrically coupled to at least one of the upstream resistive element, the downstream resistive element, or the heating element.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
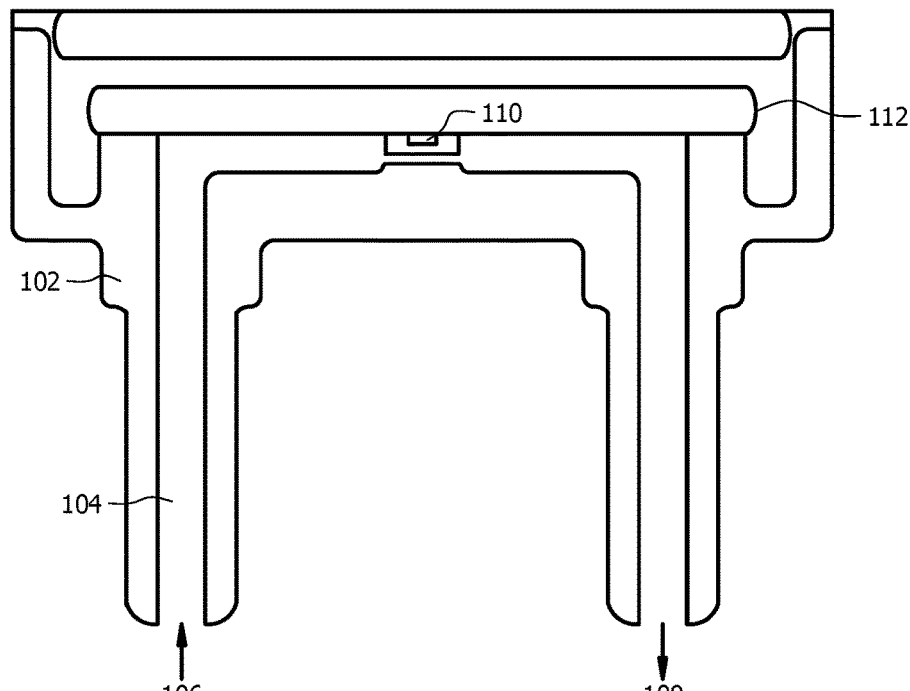
FIG. 1 illustrates a schematic cross-sectional view of an example flow sensing device.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include methods and systems for determining one or more thermal properties of a fluid flowing using an electrochemical sensor. Conventional thermal based MEMS flow sensors may measure the mass flow of a known gas or known mixture of gases. If the gas composition varies, or is unknown, it may not be possible to determine the actual flow of the gas without additional information. However, if the thermal conductivity and diffusivity of a gas are known, it may be possible to correct the mass flow values, even if the identity of the gas is unknown. Embodiments of the disclosure include a cost-effective, small and low power thermal conductivity and diffusivity sensor to allow for correction of conventional mass flow sensors, where the sensor may be integrated into a conventional mass flow sensor or may be used concurrently with a conventional mass flow sensor.

Embodiments of the disclosure may include adding additional circuitry to a central-heater mass flow sensor to gather additional information about the gas surrounding the sensor. When the heater circuit is powered by a constant direct current (DC) voltage, and the current required to maintain this voltage may be measured, the power dissipation of the heater may be determined. As the airflow sense element has been designed to minimize heat dissipation in the element itself, this power dissipation correlates well to the thermal conductivity of the gas surrounding the heater (wherein the thermal conductivity is a measure of how the gas dissipates the heat away from the heater). Additionally, if the supply voltage to the heater element is pulsed (e.g. with one of a square, sine, or similar waveform), and carefully timed measurements are taken to quantify the rate of rise in temperature at the sensing resistors, the thermal diffusivity of the gas surrounding the sensor can be inferred.

To qualify the rate of rise in temperate at the sensing resistors, one or more temperature-stable resistors, $R_{tail-1}$ and $R_{tail-2}$ in the below figures, may be connected to a conventional airflow sense die. If the temperature is known, the voltage across $R_{tail-2}$ is directly proportional to the heater power, which, as stated above, allows thermal conductivity to be measured, provided the sense element has been characterized using a known test gas to allow for sensor-to-sensor variation. The voltage across $R_{tail-1}$ measures the average temperature of the sensing resistors, and when the heater voltage is changed rapidly, as described above, the change in temperature of these resistors allows thermal diffusivity to be measured. In some embodiments, calibration and/or characterization with a known test gas may be performed on the sensor.

FIG. 1 is a schematic cross-sectional view of an example flow sensing device 100. The illustrative flow sensing device 100 includes a flow sensing device body 102 that defines a flow channel 104 having a first end 106 and a second end 108.

A fluid may flow through the flow channel 104 from, for example, the first end 106 to the second end 108 and past a flow sensor 110. The flow sensor 110 may sense the flow of the fluid passing over the flow sensor 110 and provide one or more output signals indicative of that flow. In some cases, the flow sensor 110 may provide one or more output signals that identity the flow rate of the fluid passing over the flow sensor 110.

While not required, the flow sensor 110 may include a flow sensor die that is mounted to a substrate 112. The substrate 112 may be mounted in the flow sensing device body 102. In some cases, some of the support circuitry for the flow sensor die may be located on the substrate 112 and/or may be located outside of the flow sensing device 100 altogether (e.g., located in a device that uses the output of the flow sensing device 100). FIG. 1 shows one example configuration of a flow sensing device. It should be recognized that such flow sensor devices can and do assume a wide variety of different configurations, depending on the application.

Figure 2:
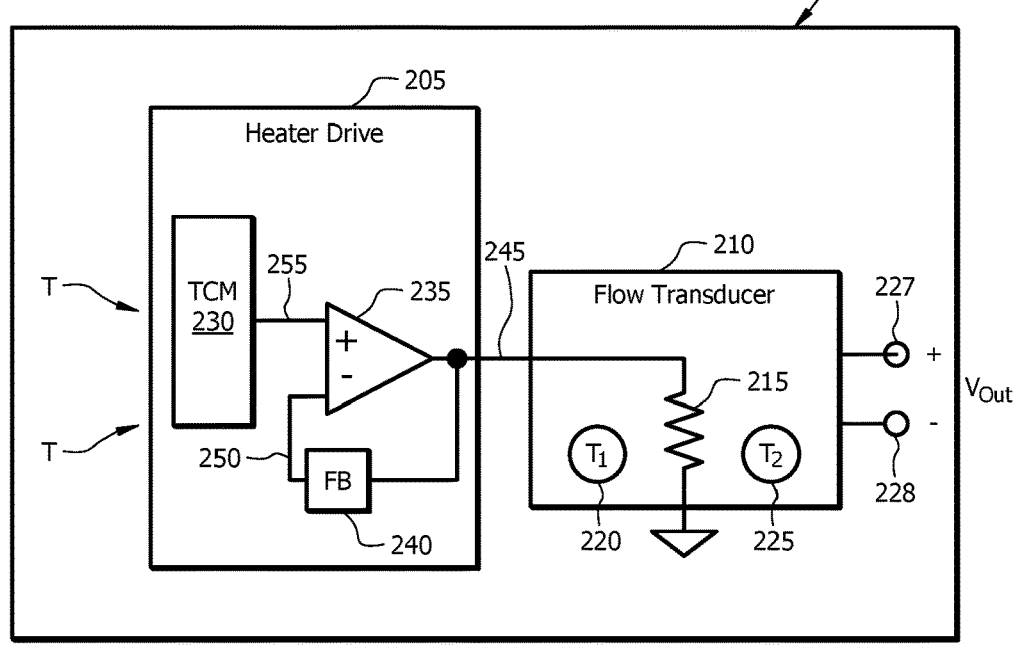
FIG. 2 illustrates a block diagram of an exemplary flow sensing device.

FIG. 2 illustrates a block diagram of an exemplary temperature-compensated fluid flow measurement system 200. The fluid flow measurement system 200 includes a heater drive circuit 205 and a fluid flow transducer 210. The flow transducer 210 has a heater 215 located between a first temperature sensor 220 and a second temperature sensor 225. Power for the heater 215 is supplied by a heater drive circuit 205. When a flow transducer 210 is introduced into a fluid material, such as a gas or liquid material, the heater 215 may be in thermal conduction with the fluid material. In some embodiments, the fluid material may substantially surround the heater 215. In some embodiments, the fluid material may pass directly over the heater 215. When the flow transducer is introduced into a fluid material, the temperature sensors 220, 225 may be in thermal communication with the fluid material. In this way, the temperature sensors 220, 225 may be in convective connection with the heater 215. The measurements of the temperature sensors 220, 225 may be indicative of a flow of the fluid material. The flow transducer 210 may put a signal indicative of a flow of the fluid material on one or more output pins 227, 228.

The heater drive circuit 205 includes a temperature-compensation module 230, an amplifier 235, and a feedback network 240. In some embodiments, the amplifier 235 may have a gain greater than one. In some embodiments, the amplifier's gain may be less than or equal to one. The amplifier 235 has an output node 245, which is connected to the heater 215 of the flow transducer 210. The feedback network 240 samples a signal on the output node 245 and may perform signal processing operations to the signal, such as may be performed by passive impedance networks, in some embodiments. The processed output signal is then delivered to a negative input node 250 of the amplifier 235 in this example. The Temperature-Compensation Module (TCM) 230 may generate a temperature-varying signal and then may deliver this temperature-varying signal to the positive input node 255 of the amplifier 235. The temperature-varying signal may be used to compensate for a disturbance due to the temperature variation of the fluid material. A temperature profile of the temperature-varying signal may be predetermined in some embodiments. In an exemplary embodiment, the temperature profile may be programmable. In various embodiments, the temperature profile may be trimmable, for example.

In an embodiment, a sensor may be used to determine the flow rate of a fluid (or gas). In some embodiments, the content of the fluid may be unknown, so it may be helpful to determine one or more characteristics or properties of the unknown fluid. The unknown fluid could be air, argon, nitrogen, methane, oxygen, etc. To accurately sense the flow rate of the unknown fluid, a sensor may be developed that is configured to self-calibrate the sensor's readings based on the fluid content. The fluid content may be approximated based on determined thermal properties of the fluid. For example, the actual identity of the fluid may be determined and/or the thermal properties may be associated with a multiplier or other correction factor that may be applied to the sensor reading.

Figures 3, 4:
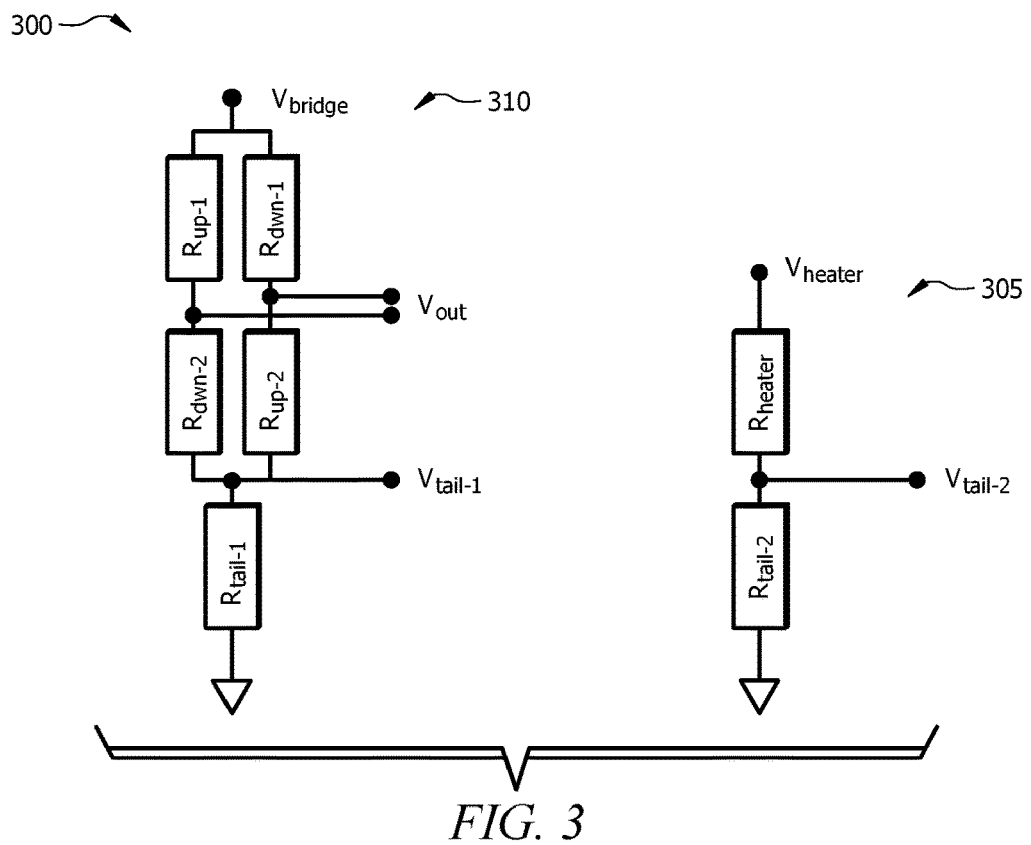
FIG. 3 illustrates a schematic circuit diagram of a flow sensor configured to determine thermal properties of a fluid.
FIG. 4 illustrates a schematic circuit diagram of a sensor configured to determine thermal properties of a fluid.

FIG. 3 illustrates a circuit diagram 300 comprising a bridge circuit 310 and a heater circuit 305 that may be incorporated into the sensor. In some embodiments, the circuit 300 may be configured to determine thermal properties of the fluid concurrently with determining the flow rate of the fluid. The bridge circuit 310 may comprise at least one upstream resistive element $R_{up-1}$ and at least one downstream resistive element $R_{dwn-1}$. In some embodiments, the circuit 300 may comprise a second upstream resistive element $R_{up-2}$ and a second downstream resistive element $R_{dwn-2}$. The resistive elements of the bridge circuit 310 may be balanced in their resistance values. In some embodiments, the bridge circuit 310 may also comprise a first tail resistor wherein the first tail resistor may be electrically coupled to the upstream and downstream resistive elements.

The heater circuit 305 may comprise a heating element $R_{heater}$ that may be physically located between the upstream and downstream resistive elements of the bridge circuit 310. The heater circuit 305 may also comprise a second tail resistor $R_{tail-2}$ that is electrically coupled to the heating element $R_{heater}$.

The upstream and downstream resistive elements of the bridge circuit 310 may change with temperature. The tail resistors $R_{tail-1}$ and $R_{tail-2}$ may be stable with temperature. The tail resistors may be configured to determine one or more thermal properties of a fluid that is passed over the surface of the circuit 300. The circuit 300 may be used to determine the mass flow rate of the fluid, and by determining one or more thermal properties of the fluid, the identity of the fluid may be approximated, and the volumetric flow rate may be calculated. Alternatively, a look-up table may be used where it is not necessary to identify the fluid.

The mass flow rate may be determined by the bridge 310 using one or more of the following equations:

$$\dot{Q} = 0.664 * Pr^{\frac{1}{3}} * \sqrt{Re_L} * \frac{k * A_{hot}}{L} * \Delta T +$$

$$k * \frac{A_{no-flow}}{L_{no-flow}} * \Delta T + \frac{k_{bridge} * A_{bridge}}{L_{bridge}} * \Delta T$$

$$\dot{Q} = 0.664 * \left(\frac{C_P * \mu}{k}\right)^{\frac{1}{3}} * \sqrt{\frac{\rho * u_\infty * L}{\mu}} * \frac{k * A_{hot}}{L} * \Delta T +$$

$$\frac{k * A_{no-flow}}{L_{no-flow}} * \Delta T + \frac{k_{bridge} * A_{bridge}}{L_{bridge}} * \Delta T$$

$$\dot{Q} \propto C_P^{\frac{1}{3}} * \mu^{-\frac{1}{6}} * k^{\frac{2}{3}} * \sqrt{\frac{\text{Mass Flow}}{L * A_{flow}}} * A_{hot} * \Delta T +$$

$$k * \frac{A_{no-flow}}{L_{no-flow}} * \Delta T + \frac{k_{bridge} * A_{bridge}}{L_{bridge}} * \Delta T$$

where k=gas conductivity, $C_p$=specific heat, $\mu$=viscosity, $\rho$=density, and $h_{flow}$=composite property term for Mass Flow. Heat transfer from Microbridge is mass flow dependent, but also has some additional gas property dependence. With no flow, the heat transfer is dependent on the thermal conductivity of the gas and the thermal conductivity of the microbridge structure. These equations are not intended to be precise but rather capture the overall dependencies.

To determine volumetric flow rate, the heat transfer may be restated in terms of volumetric flow using the following equation:

$$\dot{Q} \propto C_P^{\frac{1}{3}} * \mu^{-\frac{1}{6}} * k^{\frac{2}{3}} * \rho^{\frac{1}{2}} * \sqrt{\frac{\text{Volume Flow}}{L * A_{flow}}} * A_{hot} * \Delta T +$$

$$\frac{k * A_{no-flow}}{L_{no-flow}} * \Delta T + \frac{k_{bridge} * A_{bridge}}{L_{bridge}} * \Delta T$$

The bridge output may be controlled by heat transfer coefficients, for either true mass flow output or volume flow output. The heat transfer coefficients may have gas property dependence as well as geometric and flow dependencies. The dominant gas property in the heat transfer properties may be thermal conductivity, both in the mass flow dependent term and the no-flow term. The relationship between average bridge temperature and applied power gives another relationship with gas properties around the bridge. Putting a "tail" resistor on the heated bridge circuit allows for the total bridge current to be measured, and thereby the power.

As an example, when power is fed to the heating element $R_{heater}$, molecules in the fluid will transfer heat from the heating element to the upstream and/or downstream resistors, depending on the direction of the fluid flow. Additionally, heat may be dissipated by the fluid away from the heater into the air around the sensor. Thermal properties of the fluid may be determined by monitoring how the heat is transferred by the fluid.

The measure of how much heat is transferred by the fluid, or the thermal conductivity, may be determined using the second tail resistor $R_{tail-2}$, wherein the difference between the voltage supplied to the heating element $R_{heater}$ ($V_{heater}$) and voltage at the second tail resistor $R_{tail-2}$ ($V_{tail-2}$) indicates the power dissipated by the fluid flowing over the heating element $R_{heater}$. If the circuit is run at a constant voltage, the resistance of the heating element $R_{heater}$ changes rapidly as a function of temperature. Additionally, as the composition of the fluid changes, the power dissipated from the heating element $R_{heater}$ changes, and an approximately thermal conductivity of the fluid may be determined using the second tail resistor $R_{tail-2}$.

In another example, when the power to the heater is pulsed, the heat transfer from the heating element to the upstream and/or downstream resistors may occur periodically. The measure of how quickly heat is transferred by the fluid, or thermal diffusivity, may be determined using the first tail resistor $R_{tail-1}$, wherein the voltage at the first tail resistor $R_{tail-1}$ ($V_{tail-1}$) may be monitored to indicate when one of the upstream and/or downstream resistors changes with temperature from the heater. The time between when the heater is activated and when one of the resistors changes with the temperature may indicate how quickly the fluid dissipated the heat from the heater to the resistive elements. To determine an approximate thermal diffusivity for the fluid, the signal change over time may be correlated to the thermal diffusivity of the fluid, wherein a graph and/or look-up table may be generated for future use.

In some embodiments, the circuit 300 may be calibrated using air or another known fluid. As an example, the circuit 300 may be used in a sensor configured to detect natural gas.

Natural gas includes mostly methane, but may also contain other gases that can affect the thermal properties of the fluid, and therefore the sensor reading. These affects may be compensated for by also monitoring the thermal properties of the fluid and correcting the sensor reading accordingly. As another example, the circuit 300 may be used in a sensor configured to detect fluid in the medical field. Anesthesia gases may comprise mostly air with trace gases that can affect the thermal properties and therefore the sensor reading. These affects may be compensated for by also monitoring the thermal properties of the fluid, and correcting the sensor reading accordingly.

Referring now to FIG. 4, another embodiment of a circuit 400 is shown, wherein the circuit 400 comprises a bridge circuit 410 and a heater circuit 405. In some embodiments, the circuit 400 may be used concurrently with a flow sensor, wherein the circuit 400 may be configured to determine thermal properties of the fluid, but may not be configured to determine the flow rate of the fluid. The circuit 400 may function similarly to the circuit 300 described above, wherein the circuit 400 may comprise only one upstream resistive $R_1$ element and one downstream resistive element $R_2$.

In some embodiments, when the circuit 400 is used with another sensor for detecting the flow rate, the circuit 400 may be powered less frequently than the flow sensor. For example, while the flow sensor may take readings every 1 second, the circuit 400 (that is configured to determine thermal properties of the fluid) may take readings every 30 seconds. This may reduce the power usage when compared to the circuit 300 described above.

Figure 5:
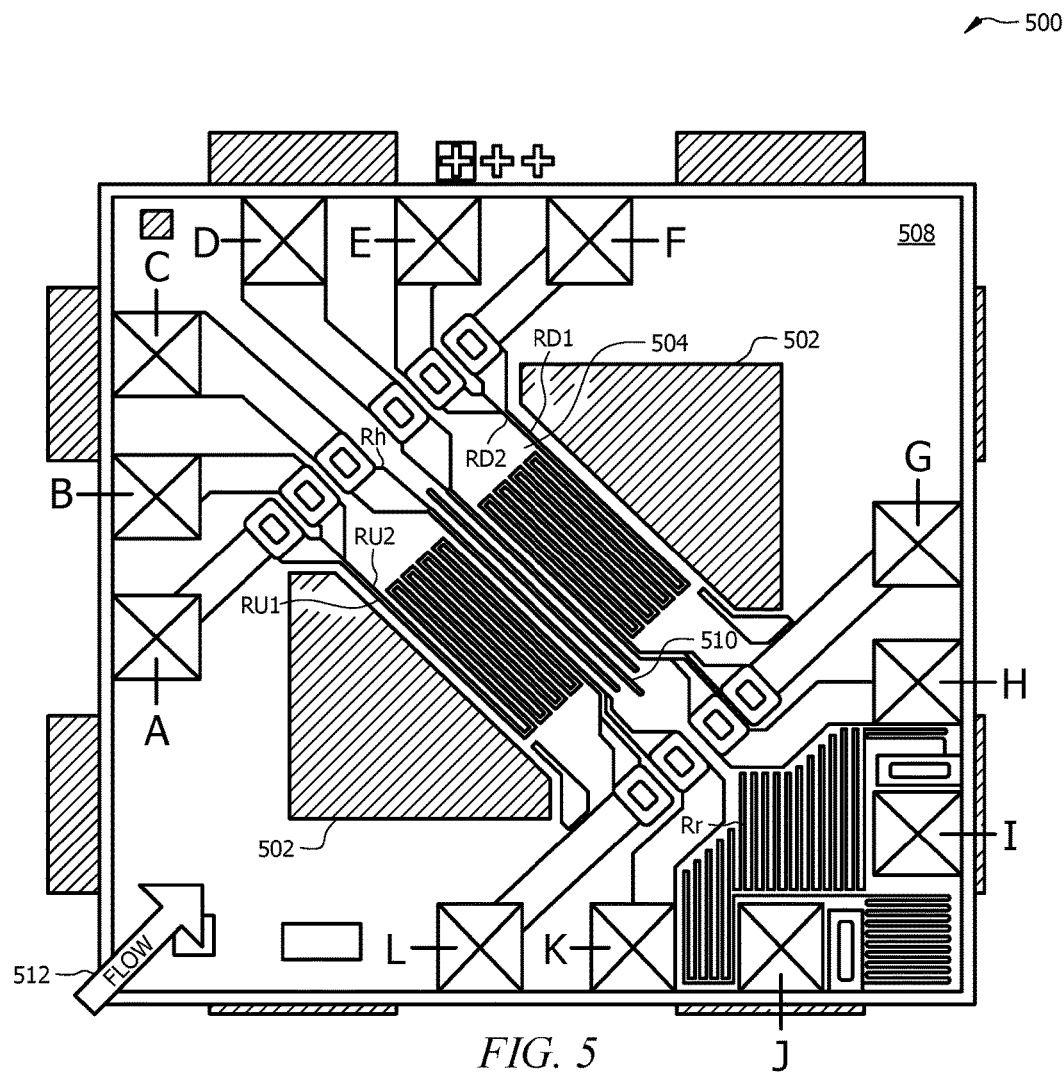
FIG. 5 is a top view of an illustrative flow sensor.

FIG. 5 is a top view of an example flow sensor die 500. The flow sensor die has an etched cavity 502 that extends under a membrane 504. The etched cavity 502 helps to thermally isolate the membrane 504 from the substrate 508 of the flow sensor die 500. The example flow sensor die 500 includes a slit 510 through the membrane 504 that extends transverse across the membrane 504. During use, the flow sensor die 500 is positioned in a flow channel.

To help explain the operation of the flow sensor die 500, it is assumed that fluid flows over the flow sensor die 500 in the direction indicated by arrow 512. When so provided, the two upstream resistive elements RU1 and RU2 are positioned on the membrane 504 upstream of the slit 510, and the two downstream resistive elements RD1 and RD2 are positioned on the membrane 504 downstream of the slit 510. The heater resistor Rh is positioned between the upstream resistive elements RU1 and RU2 and the downstream resistive elements RD1 and RD2. In the example shown, the heater resistor Rh includes two legs connected in series, with one leg positioned on either side of the slit 510. The example flow sensor die 500 is one possible layout of the schematic circuit diagrams shown in FIGS. 2-4. This example flow sensor die 500 is considered a test die, and these connections are intended to be made external to the flow sensor die 500. However, they could be made on the flow sensor die 500 if desired.

In a first embodiment, a sensor for sensing a thermal property of a fluid may comprise an upstream resistive element having a first resistance that changes with temperature; a downstream resistive element having a second resistance that changes with temperature, wherein the downstream resistive element is situated downstream of the upstream resistive element in the flow direction of the fluid; and at least one tail resistor configured to determine one or more thermal properties of the fluid, wherein the upstream resistive element and the downstream resistive element are operatively connected in a bridge circuit, wherein the at least one tail resistor is stable with temperature, and wherein the at least one tail resistor is electrically coupled to at least one of the upstream resistive element or the downstream resistive element.

A second embodiment can include the sensor of the first embodiment, further comprising a heating element configured to be substantially in direct thermal coupling with the fluid flowing through the flow channel, and wherein the at least one tail resistor is electrically coupled to at least one of the upstream resistive element, the downstream resistive element, or the heating element.

A third embodiment can include the sensor of the second embodiment, wherein the at least one tail resistor is configured to measure the thermal conductivity of the fluid.

A fourth embodiment can include the sensor of the third embodiment, wherein the at least one tail resistor is electrically coupled to the heating element, and the measured voltage difference between the heating element and the tail resistor indicates the power dissipated by the fluid flowing over the heater, and therefore the thermal conductivity of the fluid.

A fifth embodiment can include the sensor of any of the first to fourth embodiments, wherein the at least one tail resistor is configured to measure the thermal diffusivity of the fluid.

A sixth embodiment can include the sensor of the fifth embodiment, wherein the at least one tail resistor is electrically coupled to the upstream resistive element and the downstream resistive element, and wherein the measured voltage difference at the tail resistor is monitored with respect to time to determine how quickly the fluid is heated by part of the bridge circuit, and wherein that measurement is related to thermal diffusivity of the fluid.

A seventh embodiment can include the sensor of the fifth or sixth embodiments, wherein the power to the bridge circuit is pulsed, and wherein the time is measured between activating the power and when one of the upstream or downstream resistive elements indicates a temperature change.

In an eighth embodiment, a method for determining one or more thermal property of a fluid may comprise assembling a bridge circuit comprising an upstream resistive element, a downstream resistive element, and at least one tail resistor electrically coupled to at least one of the upstream resistive element or the downstream resistive element; supplying power to the bridge circuit; feeding a fluid over the bridge circuit; measuring the voltage change at the tail resistor; and determining at least one thermal property of the fluid based on the measured voltage change.

A ninth embodiment can include the method of the eighth embodiment, wherein the at least one tail resistor is stable with temperature.

A tenth embodiment can include the method of the eighth or ninth embodiments, further comprising assembling the bridge circuit comprising a heating element.

An eleventh embodiment can include the method of the tenth embodiment, wherein the at least one tail resistor is electrically coupled to the heating element, and wherein measuring the voltage change at the tail resistor comprises measuring the voltage difference between the tail resistor and the heating element.

A twelfth embodiment can include the method of the tenth or eleventh embodiments, wherein determining at least one thermal property of the fluid comprises determining the thermal conductivity of the fluid.

A thirteenth embodiment can include the method of any of the eighth to twelfth embodiments, wherein measuring the voltage change at the tail resistor comprises measuring, relative to time, the voltage difference between the tail resistor and the upstream and downstream resistive elements.

A fourteenth embodiment can include the method of the thirteenth embodiment, wherein determining at least one thermal property of the fluid comprises determining the thermal diffusivity of the fluid.

A fifteenth embodiment can include the method of the any of the eighth to fourteenth embodiments, further comprising determining a fluid flow rate through the sensor; and adjusting the determined fluid flow rate based on the determined thermal property of the fluid.

In a sixteenth embodiment, a flow sensor for sensing a fluid flow rate through a flow channel may comprise a heating element configured to be substantially in direct thermal coupling with the fluid flowing through the flow channel; an upstream resistive element having a first resistance that changes with temperature; a downstream resistive element having a second resistance that changes with temperature, wherein the downstream resistive element is situated downstream of the upstream resistive element in the flow channel; and at least one tail resistor configured to indicate one or more thermal properties of fluid flowing through the flow channel, wherein the upstream resistive element and the downstream resistive element are operatively connected in a bridge circuit; the at least one tail resistor is stable with temperature; and the at least one tail resistor is electrically coupled to at least one of the upstream resistive element, the downstream resistive element, or the heating element.

A seventeenth embodiment can include the sensor of the sixteenth embodiment, wherein the at least one tail resistor is configured to measure the thermal conductivity of the fluid.

An eighteenth embodiment can include the sensor of the sixteenth or seventeenth embodiments, wherein the at least one tail resistor is electrically coupled to the heating element, and the measured voltage difference between the heating element and the tail resistor indicates the power dissipated by the fluid flowing over the heater, and therefore the thermal conductivity of the fluid.

A nineteenth embodiment can include the sensor of any of the sixteenth to eighteenth embodiments, wherein the at least one tail resistor is configured to measure the thermal diffusivity of the fluid.

A twentieth embodiment can include the sensor of any of the sixteenth to nineteenth embodiments, wherein the power to the bridge circuit is pulsed, and wherein the time is measured between activating the power and when one of the upstream or downstream resistive elements indicates a temperature change.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A sensor for sensing a thermal property of a fluid, the sensor comprising:
   an upstream resistive element having a first resistance that changes with temperature;
   a downstream resistive element having a second resistance that changes with temperature, wherein the downstream resistive element is situated downstream of the upstream resistive element in the flow direction of the fluid; and
   at least one tail resistor configured to determine one or more thermal properties of the fluid,
   wherein:
      the upstream resistive element and the downstream resistive element are operatively connected in a bridge circuit,
      the at least one tail resistor is stable with temperature, and
      the at least one tail resistor is electrically coupled to at least one of the upstream resistive element or the downstream resistive element.

2. The sensor of claim 1, further comprising a heating element configured to be substantially in direct thermal coupling with the fluid flowing through a flow channel, and wherein the at least one tail resistor is electrically coupled to at least one of the upstream resistive element, the downstream resistive element, or the heating element.

3. The sensor of claim 2, wherein the at least one tail resistor is configured to measure the thermal conductivity of the fluid.

4. The sensor of claim 3, wherein the at least one tail resistor is electrically coupled to the heating element, and the measured voltage difference between the heating element and the tail resistor indicates the power dissipated by the fluid flowing over the heating element, and therefore the thermal conductivity of the fluid.

5. The sensor of claim 1, wherein the at least one tail resistor is configured to measure the thermal diffusivity of the fluid.

6. The sensor of claim 5, wherein the at least one tail resistor is electrically coupled to the upstream resistive element and the downstream resistive element, and wherein the measured voltage difference at the tail resistor is monitored with respect to time to determine how quickly the fluid is heated by part of the bridge circuit, and wherein that measurement is related to thermal diffusivity of the fluid.

7. The sensor of claim 5, wherein the power to the bridge circuit is pulsed, and wherein the time is measured between activating the power and when one of the upstream or downstream resistive elements indicates a temperature change.

8. A method for determining one or more thermal property of a fluid, the method comprising:
   assembling a bridge circuit comprising an upstream resistive element, a downstream resistive element, and at least one tail resistor electrically coupled to at least one of the upstream resistive element or the downstream resistive element;
   supplying power to the bridge circuit;
   feeding the fluid over the bridge circuit;
   measuring the voltage change at the tail resistor; and
   determining at least one thermal property of the fluid based on the measured voltage change.

9. The method of claim 8, wherein the at least one tail resistor is stable with temperature.

10. The method of claim 8, further comprising assembling the bridge circuit comprising a heating element.

11. The method of claim 10, wherein the at least one tail resistor is electrically coupled to the heating element, and wherein measuring the voltage change at the tail resistor comprises measuring the voltage difference between the tail resistor and the heating element.

12. The method of claim 10, wherein determining the at least one thermal property of the fluid comprises determining the thermal conductivity of the fluid.

13. The method of claim 8, wherein measuring the voltage change at the tail resistor comprises measuring, relative to time, the voltage difference between the tail resistor and the upstream and downstream resistive elements.

14. The method of claim 13, wherein determining the at least one thermal property of the fluid comprises determining the thermal diffusivity of the fluid.

15. The method of claim 8, further comprising:
   determining a fluid flow rate through a sensor; and
   adjusting the determined fluid flow rate based on the determined thermal property of the fluid.

16. A flow sensor for sensing a fluid flow rate through a flow channel, the flow sensor comprising:
   a heating element configured to be substantially in direct thermal coupling with fluid flowing through the flow channel;
   an upstream resistive element having a first resistance that changes with temperature;
   a downstream resistive element having a second resistance that changes with temperature, wherein the downstream resistive element is situated downstream of the upstream resistive element in the flow channel; and
   at least one tail resistor configured to indicate one or more thermal properties of the fluid flowing through the flow channel,
   wherein:
      the upstream resistive element and the downstream resistive element are operatively connected in a bridge circuit;
      the at least one tail resistor is stable with temperature; and
      the at least one tail resistor is electrically coupled to at least one of the upstream resistive element, the downstream resistive element, or the heating element.

17. The sensor of claim 16, wherein the at least one tail resistor is configured to measure the thermal conductivity of the fluid.

18. The sensor of claim 16, wherein the at least one tail resistor is electrically coupled to the heating element, and the measured voltage difference between the heating element and the tail resistor indicates the power dissipated by the fluid flowing over the heating element, and therefore the thermal conductivity of the fluid.

19. The sensor of claim 16, wherein the at least one tail resistor is configured to measure the thermal diffusivity of the fluid.

20. The sensor of claim 16, wherein the power to the bridge circuit is pulsed, and wherein the time is measured between activating the power and when one of the upstream or downstream resistive elements indicates a temperature change.

* * * * *